United States Patent [19]

Di Schiena et al.

[11] Patent Number: 5,047,409
[45] Date of Patent: Sep. 10, 1991

[54] COMPOUNDS FOR COSMETIC-DERMATOLOGICAL USE AND RELEVANT COMPOSITIONS

[75] Inventors: Michele G. Di Schiena; Vittoria Orrù, both of Trezzano sul Naviglio, Italy

[73] Assignee: Serono OTC S.A., Switzerland

[21] Appl. No.: 866,069

[22] Filed: May 21, 1986

[30] Foreign Application Priority Data

May 22, 1985 [IT] Italy ............................ 20837 A/85

[51] Int. Cl.$^5$ .................. C07D 239/48; A61K 31/505
[52] U.S. Cl. .................................... 514/275; 514/237; 514/256; 424/47; 424/70; 544/323; 544/123; 544/295; 544/298
[58] Field of Search ............... 544/323, 123, 295, 298; 424/47, 70; 514/275, 237, 256

[56] References Cited

U.S. PATENT DOCUMENTS 3,461,461   8/1969   Anthony et al. ................ 544/123
4,139,619   2/1979   Chidsey ........................... 514/275
4,596,812   6/1986   Chidsey et al. ................. 514/256

OTHER PUBLICATIONS

Fruton and Simmonds, "General Biochemistry", 2nd Edition, pp. 59–60, (1961).

Primary Examiner—John M. Ford
Attorney, Agent, or Firm—Ostrolenk, Faber, Gerb & Soffen

[57] ABSTRACT

Salts of thiazolidine-4-carboxylic acids with 6-Piperidino-2,4-diaminopyrimidine-3-oxide are described of Formula I.

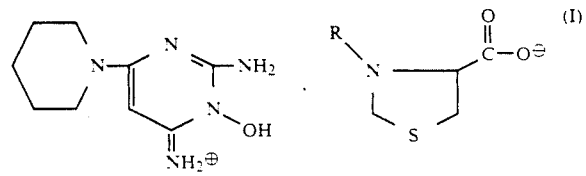

Compounds I are useful in the field of cosmetics and pharmaceuticals for the treatment of loss of hair or in pathological forms such as alopecia, flaking dermatitis, etc. . . . Topical formulations containing compounds I are also described.

10 Claims, No Drawings

COMPOUNDS FOR COSMETIC-DERMATOLOGICAL USE AND RELEVANT COMPOSITIONS

SUMMARY

Salts of thiazolidine-4-carboxylic acids with 6-piperidino-2,4-diaminopyrimidine-3-oxide are described, of Formula I

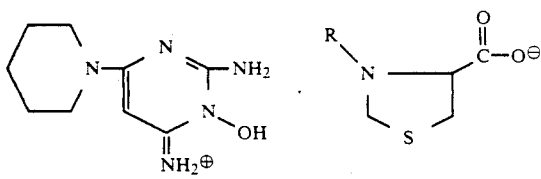

Compounds I are useful in the field of cosmetics and pharmaceuticals for the treatment of loss of hair or in pathological forms such as alopecia, flaking dermatitis, etc . . . Topical formulations containing compounds I are also described.

DESCRIPTION OF THE INVENTION

Object of the present invention are the salts of thiazolidine-4-carboxylic acids with 6-piperidino-2,4-diaminopyrimidine-3-oxide, of Formula I

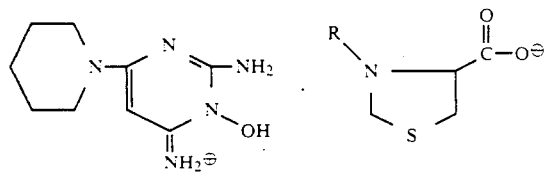

wherein R represents: hydrogen: an aromatic or aliphatic acylic residue: an acylic residue either deriving from an aminoacid or from a bicarboxylic acid: an alkylic or cycloalkylic, even unsaturated residue: an arylic, aralkylic or alkylarylic residue: or an alkyloxy or aryloxycarbonyl residue.

Examples of acylic residues include formyl, acetyl, trifluoroacetyl, propionyl, butyryl, hexanoyl, pivaloyl, caproyl, lauroyl, stearoyl, pharyleatyl, benzoyl, 3,4,5-trimethoxybenzoyl, cyclopentacarbonyl, 4-aminobenzoyl, 2,3- or 4-chlorobenzoyl, 2,3,4-methyl-benzoyl: amino acyl residues deriving from glycine, alanine, valine, lysine, aspartic acid, histidine, cysteine, etc. . . : acyl residues deriving from bicarboxylic acids such as malonic, succinic, malic, maleic, fumaric, glutaric, adipic, cyclohexam-1,4-dicarboxylic, camphoric, endobicyclo (2.2.2) ott-5-en-2,3-dicarboxylic, phthalic, terephthalic, isophthalic acids. Examples of alkylic residues include methyl, ethyl, n-propyl, i-propyl, n-butyl, sec-butyl, t-butyl, n-pentyl, neopentyl, n-hexyl, cyclohexyl, cyclopentyl, 4-methylcyclohexyl.

Examples of arylic, alkylarylic or aralkylic residues include phenyl, benzyl, 2,3- or 4-tolyl, eventually substituted by halogen atoms, OH, $OCH_3NH_2$, $NO_2$, $CH_3$, or $CF_3$.

Finally, examples of alkyloxy- or aryloxy-carbonyl residues include t-butyloxycarbonyl, ethyloxycarbonyl, benzyloxycarbonyl, 2,2,2-trichloro-ethyloxycarbonyl.

A compound I which is particularly preferred is that wherein R is acetyl, hereinafter indicated briefly under the code MT/2.

Compounds I are endowed with activities that favour the growth of hair and other body hairs and may therefore be utilized in the field of cosmetics or pharmaceuticals in the forms of suitable topical formulations.

The derivative of 2,4-diaminopyrinidine, which constitutes the basic component of the salts of Formula I is also known under the International non-proprietary name minoxidil: it is currently used in human therapy as an anti-hypertensive and recently its use has been described for topical application in the treatment of common baldness and aerated alopecia.

Due to the insolubility of minoxidil in water, its liquid formulations are based on glycols and polyalcohols, and are consequently unpleasant for topical use as they tend to make the scalp oily.

The salts, object of the invention, are on the contrary hydrosoluble and may be easily formulated in watery based compositions.

The acid compounds of the salts of Formula I are derivatives of thiazolidine-4-carboxylic acid or thioproline (also known as timonacic acid).

Thioproline, which may be in L, D, or DL form, is currently used for topical treatment of functional alterations and poor condition of hair, scalp and body hairs in general.

Thioproline and its derivatives act as donors of reactive thiol groups which operate directly on the skeleton of keratine and cellular metabolism, thus favouring the reticulation of keratinic proteins.

The resulting elevated degree of reticulation confers on keratin both mechanical stability and chemical and biological resistance. thus contributing to facilitate the growth of hair and body hairs, and to maintain their optimal condition and aspect (sheen).

Furthermore, the freed thiol groups, by reacting with the sulphur bonds of keratin, render the dried corneous stratus more flexible and the superficial stratus partially soluble so that it may be easily eliminated simply by washing: the typical flaking that occurs in case of dandruff is therefore prevented.

Differently from other compounds which provide thiol groups, thioproline and derivatives are stable to auto-oxidation even in solution.

It has been discovered that salts I, particularly compound MT/2, are therapeutically superior to minoxidil, alone and show a marked synergism between the two components.

Both systemic toxicity and cutaneous tolerability of MT/1 are within the known values for minoxidil alone when administered topically.

Consequently, compounds I due to their biological properties and hydrosolubility can advantageously be formulated in lotions, creams, sprays, shampoo, gel, brilliantine, and hair fixers preferably in an exclusively watery base or a prevalently watery base.

The formulations, object of the invention, besides one or more of the compounds of formula I, may contain other active principles with complementary activity as well as conventionally used vehicles and excipients such as fragrances, stabilizers, dyes, etc . . .

The formulations of the invention have a concentration of the active principle varying from 0.1 to 10% and will generally be applied on the skin to be treated once or twice a day.

Preparation of the new compounds uses techniques already known in the art: for example they may be easily prepared in water by making minoxidil react with N-acetyl-thioproline in a practically unitary stechiometric ratio.

The compounds of the invention may be easily prepared by using other suitable solvents such as methanol, ethanol, isopropanol, etc.

Compounds I are isolated by using conventional techniques, for example, evaporation of the solvent, precipitation with non-solvents, etc.

The examples that follow are useful only for illustrating the invention and should not be construed in any way as a limitation of it.

EXAMPLE 1

1.8 g of N-acetyl-thioproline are added to a suspension of 2 g of minoxidil in 50 ml of water.

The obtained solution can be used as such for the preparation of compositions suitable for topical application.

The compound can be alternatively isolated in a solid form, for example, by evaporation of water preferably at low pressure.

The compound of Formula I thus obtained, when chemically tested is, perfectly pure as shown by its IR spectrum.

EXAMPLE 2

2.09 g of minoxidil and 4.75 g of N-acetyl-thioproline are disolved in 100 ml of 95% ethanol. The obtained solution may be used as such or suitably diluted and/or coadjuvant or complementary substances may be added.

The solid compound can be alternatively isolated by total evaporation of the solvent or partial evaporation and the subsequent addition of ethyl ether as an insolubilizing agent.

The solid obtained corresponds chemically to that obtained in Example 1.

EXAMPLE 3

Analogous to the previous examples, but substituting N-acetyl-thioproline with other N-acyl derivatives, the following salts are obtained:
Minoxidil N-Pivaloyl-thiazolidine-4-carboxylate:
Minoxidil N-Phthaloyl-thiazolidine-4-carboxylate:
Minoxidil N-Benzoyl-thiazolidine-4-carboxylate:
Minoxidil N-Glycyl-thiazolidine-4-carboxylate:
Minoxidil N-Formyl-thiazolidine-4-carboxylate.

EXAMPLE 4

1.33 g of thiazolidine-carboxylic acid and 2.09 g of minoxidil in 50 ml of methanol and 20 ml of $H_2O$ are brought to reflux for one hour. The solvent is evaporated in a vacuum. The residue is composed of the salts of thiazolidine-carboxylate of minoxidil. IR analysis confirms the assigned structure. TLC analysis confirms the purity of the compound.

EXAMPLE 5

Formulations

Some compositions of formulations of the salts prepared according to Examples 1 or 2 are reported as follows:
a) Lotion
MT/2—3.84 g
Sodium ascorbate—0.5 g
Preservative—q.s.
Perfumed and coloured water—q.s. to 100 g b) Lotion
MT/2—3.84 g
Vitamin H—1 g
Inosite (R)—1 g
Calcium Pantothenate—1 g
Amino acid complex—0.2 g
Vitamin B complex—5 g
Isopropyl alcohol—520 g
Perfumed water—q.s. to 1000 g
c) Lotion
MT/2—3.84 g
Ucon (R) 75-H-450—10 g
Vancide (R) 89 RE—0.1 g
Fragrance—q.s.
Ethyl alcohol 95 degrees—50 g
Water—q.s. to 100 g
d) Aerosol Lotion
MT/2—3.84 g
Panthenol—1 g
Lanogel 21 (R)—0.5 g
Zelek MK (R) (antistatic)—0.1 g
Fragrance—q.s.
Alcohol—25 g
Freon (R) 11/12 (60.40)—70 g
e) Lotion
MT/2—3.84 g
Alcohol—30 g
Fragrance—traces
Colour—q.s.
Water—q.s. to 100 g
f) Lotion
MT/2—3.84 g
Resorcin—5 g
Tincture of capsicum—5 g
Ricin oil—5 g
Alcohol 90 degrees—q.s. to 100 g
Fragrance—q.s.
g) Lotion
MT/2—3.84 g
Betanaphthol—0.5 g
Glycerin—5 g
Alcohol 90 degrees—50 g
Fragrance—q.s.
Water—q.s. to 100 g
h) Lotion
MT/2—3.84 g
Isopropyl alcohol—50 g
Fragrance—q.s.
Salicylic acid—0.2 g
Water—q.s. to 100 g
i) Aerosol Foam Lotion
MT/2—3.84 g
Cetyl alcohol—0.8 g
Sapogenat T/100 (R)—0.2 g
Neo-Extrapon H (R)—2 g
Iso-Adipat (R)—1 g
Neo-PCL, hydrosoluble (R)—2 g
Menthol—0.2 g
Emulsogen OG (R)—2 g
Hostaphat KL.340 (R)—2.5 g
Ethyl alcohol—45 g
Fragrance—1.2 g
Water—q.s. to 100 g
To fill: the above formula—85 g
Propellent: 12/114 (10:60)—15 g
j) Cream
MT/2—3.84 g
Diglycol stearate—12 g Triethanolamine stearate—5 g
Lanolin—4 g
Cholesterin—5 g
Lecithin—0.5 g
Diethyl sebacate—0.5 g
Isopropyl myristate—10 g
Preservative—q.s.
Water—63 g
k) Shampoo
MT/2—3.84 g
Saccharose monolaurate—50 g
Fragrance and colour—q.s.
Water—q.s. to 100 g
l) Hair Fixer
MT/2—3.84 g
Sodium alginate—1.2 g
Calcium citrate—0.1 g
Alcohol—3 g
Fragrance—q.s.
Preservative—q.s.
Water—q.s. to 100 g

We claim:
1. A salt of a thiazolidine-4-carboxylic acid with 6-piperidino-2,4-diaminopyrimidine-3-oxide of the formula

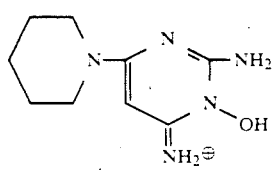 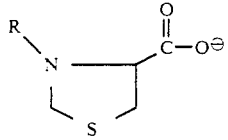

wherein R is hydrogen, formyl, acetyl, trifluoroacetyl, propionyl, butyryl, hexanoyl, pivaloyl, caproyl, lauroyl, stearoyl, phthaloyl, benzoyl, 3,4,5-trimethoxybenzoyl, cyclopentacarbonyl, 4-aminobenzoyl, 2,3- or 4-chlorobenzoyl, 2,3,4-methyl-benzoyl, glycyl, alanyl, valyl, lysyl, aspartyl, histidyl, cysteyl, malonyl, succinyl, malyl, maleyl, fumaryl, glutaryl, adipyl, cyclohexam-1,4-dicarboxyl, camphoryl, endobicyclo (2.2.2) ott-5-en-2,3-dicarboxyl, phthalyl, terephthalyl, isophthalyl, methyl, ethyl, n-propyl, i-propyl, n-butyl, sec-butyl, t-butyl, n-pentyl, neopentyl, n-hexyl, cyclohexyl, cyclopentyl, 4-methylcyclohexyl, t-butyloxycarbonyl, ethyloxycarbonyl, benzyloxycarbonyl, 2,2,2-trichloroethyloxycarbonyl and aryl or halo, OH, OCH$_2$, OCH$_3$, NH$_2$, NO$_2$, CH$_3$, or CF$_3$ substituted aryl in which said aryl radical is phenyl, benzyl or tolyl.

2. The salt of claim 1 wherein R is hydrogen, pivaloyl, phthaloyl, benzoyl, glycyl or formyl.

3. The salt of claim 1 wherein R is acetyl.

4. The salt according to claim 3 wherein said thiazolidine moiety is N-acetyl-L-4-thiazolidine carboxylate.

5. A composition for topical use in trichology comprising 0.1 to 10% by weight of a salt of claim 1 and a topical vehicle therefor.

6. The composition of claim 5 in which the vehicle is an aqueous vehicle.

7. The composition of claim 5 wherein R is hydrogen, pivaloyl, phthaloyl, benzoyl, glycyl or formyl.

8. The composition of claim 5 wherein R is acetyl.

9. The composition according to claim 8 wherein said thiazolidine is N-acetyl-L-4-thiazolidine carboxylate.

10. The composition according to claim 5 wherein said vehicle is a lotion, shampoo, hair fixer, cream or spray vehicle.

* * * * *